US007078029B2

(12) United States Patent
DeLuca

(10) Patent No.: US 7,078,029 B2
(45) Date of Patent: *Jul. 18, 2006

(54) HERPES SIMPLEX VIRUS STRAINS

(75) Inventor: Neal A. DeLuca, Cheswick, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 456 days.

This patent is subject to a terminal disclaimer.

(21) Appl. No.: 10/427,739

(22) Filed: May 1, 2003

(65) Prior Publication Data

US 2003/0206888 A1    Nov. 6, 2003

Related U.S. Application Data

(63) Continuation of application No. 09/829,839, filed on Apr. 10, 2001, now abandoned, which is a continuation of application No. 09/194,274, filed as application No. PCT/US97/08681 on May 22, 1997, now Pat. No. 6,261,552.

(51) Int. Cl.
 *A61K 48/00* (2006.01)
 *C12N 15/00* (2006.01)
 *C12N 15/64* (2006.01)

(52) U.S. Cl. .................. 424/93.2; 435/320.1; 435/325; 435/91.41; 435/91.42; 435/455

(58) Field of Classification Search .................. None
See application file for complete search history.

(56) References Cited

U.S. PATENT DOCUMENTS

| 5,026,635 A | 6/1991 | Ferguson et al. |
| 5,070,010 A | 12/1991 | Hsu |
| 5,124,263 A | 6/1992 | Temin et al. |
| 5,658,724 A | 8/1997 | DeLuca |
| 5,672,344 A | 9/1997 | Kelley et al. |
| 5,674,722 A | 10/1997 | Mulligan et al. |
| 5,804,413 A | 9/1998 | DeLuca |

FOREIGN PATENT DOCUMENTS

EP    0 453 242 A1    10/1991
WO    WO 95/13391 A1    5/1995
WO    WO 96/24663 A1    8/1996

OTHER PUBLICATIONS

Mackem et al., Journal of Virology, 44:939-949 (1982).*
Misra V et al., Journal of Virology, 68:4898-4909 (1994).*
Pizer Li et al., Nucleic Acids Research, 19:477-483 (1991).*
Post Le et al., Cell 25:227-232 (1981).*
Resnick J et al., ournal of Virology 63:2497-2503 (1989).*
Batchelor et al., *Journal of Virology*, 64(7), 3269-3279 (1990).
Breakefield et al., *The New Biologist*, 3(3), 203-218 (1991).
Breakefield et al., *Treatment of Genetic Diseases*, (*Desnick ed.*), 287-319 (1991).
Chiocca et al., *The New Biologist*, 2(8), 739-746 (1990).
Croen et al., *New England Journal of Medicine*, 317(23), 1427-1432 (1987).
DeLuca et al., *Journal of Virology*, 56(2), 558-570 (1985).
DeLuca et al., *Nucleic Acids Research*, 15(11), 4491-4511 (1987).
DeLuca et al., *Journal of Virology*, 62(3), 732-743 (1988).
Dobson et al., *Journal of Virology*, 63(9), 3844-3851 (1989).
Dobson et al., *Neuron*, 5(3), 353-360 (1990).
Douville et al., *Virology*, 207(1), 107-116 (1995).
Glorioso et al., *Seminars in Virology*, 3(4), 265-276 (1992).
Goins et al., *Journal of Virology*, 68(4), 2239-2252 (1994).
Ho et al., *Proceedings of the National Academy of Sciences of the United States of America*, 86(19), 7596-7600 (1989).
Imbalzano et al., *Journal of Virology*, 65(2), 565-574 (1991).
Johnson et al., *Journal of Virology*, 65(5), 2952-2965 (1992).
Johnson et al., *Journal of Virology*, 68(10), 6347-6362 (1994).

(Continued)

*Primary Examiner*—Janet L. Epps-Ford
*Assistant Examiner*—Maria Leavitt
(74) *Attorney, Agent, or Firm*—Leydig, Voit & Mayer, Ltd.

(57) ABSTRACT

The present invention provides an HSV having a genome with a mutation of a TAATGARAT sequence such that, in the presence of a ICP4 gene product, a native immediate early gene is expressed from the genome with delayed kinetics, the genome having a further inactivating mutation of each of the genes encoding ICP4.

30 Claims, 8 Drawing Sheets

OTHER PUBLICATIONS

Kmetz et al., *Nucleic Acids Research*, 16(10), 4735 (1988).
Krisky et al., *Gene Therapy*, 5, 1593-1603 (1998).
Lokensgard et al., *Journal of Virology*, 68(11), 7148-7158 (1994).
McCarthy et al. ,*Journal of Virology*, 63(1), 18-27 (1989).
Ngo et al., *The Protein Folding Problem and Tertiary Structure Prediction*, (Merz et al. eds.), 434-506 (1994).
Orkin et al., *Report and Recommendations of the Panel to Assess the NIH Investment in Research on Gene Therapy*, 1-39 (1995).
Paterson et al., *Nucleic Acids Research*, 16(23), 11005-11025 (1988).
Paterson et al., *Virology*, 166(1), 186-196 (1988).
Post et al., *Cell*, 25, 227-232 (1981).
Rivera-Gonzalez et al., *Virology*, 202(2), 550-564 (1994).
Roizman et al., *Virology*, (Fields ed.), 497-526 (1985).
Sacks et al., *Journal of Virology*, 55(3), 796-805 (1985).
Sacks et al., *Journal of Virology*, 61(3), 829-839 (1987).
Samaniego et al., *Journal of Virology*, 69(9), 5705-5715 (1995).
Samaniego et al., *Journal of Virology*, 71(6), 4614-4625 (1997).
Samaniego et al., *Journal of Virology*, 72(4), 3307-3320 (1998).
Sears et al., *Journal of Virology*, 55(2), 338-346 (1985).
Shepard et al., *Journal of Virology*, 65(2), 787-795 (1991).
Shih et al., *Proceedings of the National Academy of Sciences of the United States of America*, 81(18), 5867-5870 (1984).
Spector et al., *Journal of Virology*, 3504-3513 (1991).
Walker et al., *Cell*, 79(5), 841-852 (1994).
Werstuck et al., *Journal of Virology*, 64(3), 984-991 (1990).
Wu et al., *Journal of Virology*, 70(9), 6358-6369 (1996).
Shepard et al., "Separation of Primary Structural Components Conferring Autoregulation, Transactivation, and DNA-Binding Properties to the Herpes Simplex Virus Transcriptional Regulatory Protein ICP4," *Journal of Virology*, 63(9): 3714-3728 (Sep. 1989).
Bandyopadhyay et al., "Expression from an Internal AUG Codon of Herpes Simplex Thymidine Kinase Gene Inserted in a Retrovirus Vector," *Molecular and Cellular Biology*, 4(4): 743-748 (Apr. 1984).
Shepard et al., "Separation of Primary Structural Components Conferring Autoregulation, Transactivation, and DNA-Binding Properties to the Herpes Simplex Virus Transcriptional Regulatory Protein ICP4," *Journal of Virology*, 63(9): 3714-3728 (Sep. 1989).
Bandyopadhyay et al., "Expression from an Internal AUG Codon of Herpes Simplex Thymidine Kinase Gene Inserted in a Retrovirus Vector," *Molecular and Cellular Biology*, 4(4): 743-748 (Apr. 1984).

\* cited by examiner

HERPES SIMPLEX VIRUS STRAINS

CROSS-REFERENCE TO RELATED APPLICATIONS

This patent application is a continuation of U.S. patent application Ser. No. 09/829,839, filed Apr. 10, 2001, now abandoned, which is a continuation of application Ser. No. 09/194,274, filed on Nov. 20, 1998, now U.S. Pat. No. 6,261,552, which was a national phase of International Patent Application PCT/US97/08681, filed May 22, 1997.

TECHNICAL FIELD OF THE INVENTION

The present invention relates to herpes simplex virus strains, cell lines, methods for their production, and methods for their use.

BACKGROUND OF THE INVENTION

Herpes simplex virus (HSV) contains a double-stranded, linear DNA genome comprised of approximately 152 kb of nucleotide sequence, which encodes about 80 genes. The viral genes are transcribed by cellular RNA polymerase II and are temporally regulated, resulting in the transcription and subsequent synthesis of gene products in roughly discernible phases: Immediate Early (IE, or α), Early (E, or β) and Late (L, or γ). Immediately following the arrival of an HSV genome into the nucleus of an infected cell, the IE genes are transcribed. The IE genes are all activated by a complex including the HSV virion particle VP16 and the cellular factor, Oct-1, which binds to a consensus sequence (TAATGARAT) regulating IE gene expression (Preston et al., *Cell,* 52, 425–35 (1988)). The presence of this sequence, thus, confers the IE quality to HSV regulatory sequences. The efficient expression of IE genes, thus, does not require prior viral protein synthesis, while later expression depends upon the presence of IE gene products. The products of IE genes are required to activate transcription and regulate the remainder of the viral genome.

Infected Cell Peptide 4 (ICP4), ICP0, ICP27, ICP22, and ICP47 are the immediate early gene products, and these show varying degrees of essentiality to HSV function. These phosphoproteins possess regulatory activities thought to prime the host cell for the efficient cascade of subsequent viral gene expression, DNA replication and the production of progeny virions. The manner in which the IE gene products act in concert to effect the cascade of regulatory activity giving rise to productive infection is poorly understood. However, many functions of these gene products are known. For example, ICP0 activates most test promoters in transient assays (Quinlan and Knipe, *Mol. Cell. Biol.,* 5, 957–63 (1985)), elevates levels of viral gene expression and growth in tissue culture and in the trigeminal ganglia (Cai and Schaffer, *J. Virol.,* 66, 2904–15 (1992)), and facilitates the reactivation of virus from latency (Leib, et al., *J. Virol.,* 63, 759–68 (1989)). ICP27 modulates the activity of ICP4 and ICP0, and it regulates viral and cellular mRNA processing. These activities of ICP27 mostly contribute to efficient DNA replication, hence it is essential for viral growth; however, ICP27 also regulates the proper expression of early and late genes. ICP22 promotes efficient late gene expression in a cell-type dependent manner and is involved in the production of a novel modified form of RNA Pol II. ICP4 is a large multifunctional protein. It can act as a transcription factor that either represses or activates transcription through contacts with the general transcriptional machinery. ICP4 is absolutely required for both virus infectivity and the transition from IE to later transcription.

The activities of genes other than the IE genes also play significant regulatory roles in HSV infection. The HSV gene UL39 encodes ICP6, the large subunit of ribonucleotide reductase, a key enzyme in the pathway reducing ribonucleotides to the corresponding deoxribonucleotides. ICP6 (or UL39) is best classified as an early gene and is not essential for viral growth in dividing cells. UL41 is a late HSV gene product released during host cell infection which mediates the inhibition of host cell metabolism, including DNA and protein synthesis. This viral induced host shut-off is linked to destabilization and degradation of host mRNA.

Owing to its central role in the regulation of HSV gene expression, ICP4 has been the subject of numerous genetic and biochemical studies aimed at developing mutant viruses devoid of ICP4 activity, such as the d120 HSV virus (DeLuca, et al., *J. Virol.,* 56, 558–70 (1985); DeLuca, et al., *Nuc. Acids Res.,* 15, 4491–11 (1987); DeLuca, et al., *J. Virol.,* 62, 732–43 (1988); Paterson, et al., *Virology,* 166, 186–96 (1988); Paterson, et al., *Nuc. Acids Res.,* 16, 11005–25 (1988); Shepard, et al., *J. Virol.,* 63, 3714–28 (1989); Imbalzano, et al., *J. Virol.,* 65, 565–74 (1991); and Shepard, et al., *J. Virol.,* 65, 787–95 (1991)). One property of viruses deleted for ICP4 that makes them desirable for gene transfer is that they only express a very limited subset of HSV genes including the four other IE genes: ICP0, ICP27, ICP22 and ICP47, as well as ICP6 (DeLuca, et al., 1985, supra). This set of genes excludes genes encoding proteins that direct viral DNA synthesis, as well as the structural proteins of the virus, many of which interfere with host cell metabolism.

The phenotype of viruses lacking ICP4, suggests that such viruses could be potentially useful for gene transfer purposes (Breakefield, et al., *Treatment of Genetic Diseases,* (Churchill Livingstone, Inc., 1991); and Chocca, et al., *The New Biologist,* 2, 739–46 (1990)). Despite the fact viruses lacking ICP4 are blocked at the earliest stage of infection genetically possible subsequent to the delivery of the genome to the host cell nucleus, two phenomena have complicated the use of such viruses for effective gene transfer or therapy. First, viruses lacking essential genes, such as ICP4- or ICP27-deficient viruses, require the exogenous supply of the missing viral gene product, such as a cell line engineered to express the gene (DeLuca, 1985, supra). Homologous recombination events between the mutant viral genome and the wild-type gene resident in the host cell genome can "rescue" a population of viruses no longer deleted for that gene (Id.), particularly where the viral and host cell genomes include sequences of homology. Secondly, despite only expressing the four other immediate early proteins, ICP4-deficient viruses are toxic to infected cells. For example, infection of cells with ICP4 mutants causes chromosomal aberrations and rapid cell death (Johnson, et al., *J. Virol.,* 66, 2952–65 (1992); Peat and Stanley, *J. Gen. Virol.,* 67, 2273–77 (1986)). Moreover, either ICP4, ICP0, ICP27 or ICP22 significantly reduce the transformation efficiency of cultured cells via G418 resistance (Johnson, et al., *J. Virol.,* 68, 6347–62 (1994)). This toxicity is most probably due to the expression of one or more of the remaining immediate early proteins, rather than the incoming capsid, since defective HSV virus particles, containing intact capsids and lacking all IE genes, are not toxic. In addition, ICP4 deficient viruses shut off host cell protein synthesis through the activity of the UL41 virion gene product (Read, et al., *J. Virol.,* 67, 7149–60 (1993)).

Further work has produced an HSV vector (d92) having mutations in both essential immediate early genes (i.e., ICP4 and ICP27) using a novel cell line (26 cells) expressing both viral proteins (Samaniego et al., *J. Virol.* 69(9), 5705–15 (1996)). This viral/cell line system was engineered to minimize homology between the virus and the cell line in order to substantially reduce the probability of rescuing a wild-type revertant HSV, thus permitting the use of higher m.o.i. in gene-transfer protocols. Moreover, more persistent genomes are obtainable with d92 than with ICP4$^{(-)}$ viruses. In the absence of ICP4 and ICP27, only ICP6, ICP0, ICP22, and ICP47 are expressed from the viral genome; hence the double mutant is somewhat less cytotoxic than the single mutant. However, the expression of this set of genes renders the double mutant significantly cytotoxic, largely due to the presence of the ICP0 gene product. Despite the teachings in the art indicating that ICP0$^{(-)}$ viruses can grow in the absence of complementation (e.g., Cai and Schaffer, supra), the isolation and propagation of an HSV wherein ICP0 is deleted from an HSV genome already lacking ICP4 and ICP27 by employing a double complementing (E26 cells) cell line has not been possible. The growth-dampening effect of deleting ICP0 in a ICP4$^{(-)}$ICP27$^{(-)}$ mutant is unexpectedly greater than that observed for a wild-type background.

Therefore, a need exists for defective herpes simplex virus strains exhibiting efficient growth in a controlled laboratory complementing system, a reduced level of wild-type virus regeneration, and lowered cytotoxic effects. Concomitantly, there exists a need for a method of producing such viral strains and a cell line for propagating the same.

BRIEF SUMMARY OF THE INVENTION

The present invention provides an HSV having a genome from which, in the presence of the ICP4 gene product, a native immediate early gene is expressed with delayed kinetics, and an HSV having a genome with a mutation in each of the genes encoding ICP4, ICP27, and another HSV gene; preferably such HSV have one or more exogenous genes. The present invention further provides a method of expressing a polynucleotide within a cell comprising infecting the cell with such an HSV. Furthermore, the present invention provides a cell line having DNA encoding the HSV proteins ICP4, ICP27, and ICP0, and a method of producing an HSV vector by employing such a cell line.

These HSV mutant strains have characteristics amenable to use as gene transfer vehicles, including (1) the ability to obtain large quantities of recombinant virus, (2) a significant reduction in wild-type reversion, (3) an ability to accept larger foreign DNA fragments for gene transfer applications, (4) minimized interference with host cell protein synthesis, and (5) reduced or even minimal host cell cytotoxicity. Viral gene expression in some of these HSV strains is substantially eliminated. The generation of a viral genome that will enter the nucleus and not express any of its encoded genes profoundly reduces the cytotoxic effects associated with the expression of HSV proteins. This allows for the expression of a non-HSV gene from the HSV genome without significant cytotoxic side effects.

Thus, the vectors of the present invention are highly useful in biological research. Specifically, the present invention provides reagents and methods enabling biologists to more easily study HSV molecular genetics and cytotoxicity. Additionally, the present invention provides reagents and methods permitting biologists to investigate the cell biology of viral growth and infection. Furthermore, the vectors of the present invention equip the biologist with novel tools for investigating molecular and cellular biology of gene expression and regulation in novel genetic backgrounds. Such studies, for example, can focus on the interaction between gene products in a defined or selected cellular background, the ability of transcription factors to transregulate gene expression via promoter, repressor, or enhancer elements engineered into the HSV vector, etc.

The present invention also is highly useful in the clinical setting. Specifically, the present invention permits more efficient production and construction of safer HSV vectors for gene therapy applications.

BRIEF DESCRIPTION OF THE FIGURES

FIG. 4A presents a quantitative analysis of cellular β-tubulin RNA species after 24 hours in cells infected by several viruses. FIG. 4B presents a quantitative analysis of cellular β-tubulin RNA species at 1–3 days post infection for cells infected with d95. FIG. 4C presents a qualitative analysis of cellular β-tubulin RNA species after 24 hours in cells infected by several viruses. FIG. 4D presents a qualitative analysis of cellular β-tubulin RNA species at 1–3 days post infection for cells infected with d95.

FIG. 5A indicates cell number of d95-infected Vero cells and 1, 2, 3 and 4 days post infection.

FIG. 5B indicates cell survival as a function of m.o.i. of d50-infected, d92-infected, d95-infected Vero cells, and mock infected Vero cells.

FIG. 5C indicates the effect of d95 infection on host Vero cell DNA replication.

FIG. 5D indicates the effect of d95 infection on host HEL cell DNA replication.

Figure 1:
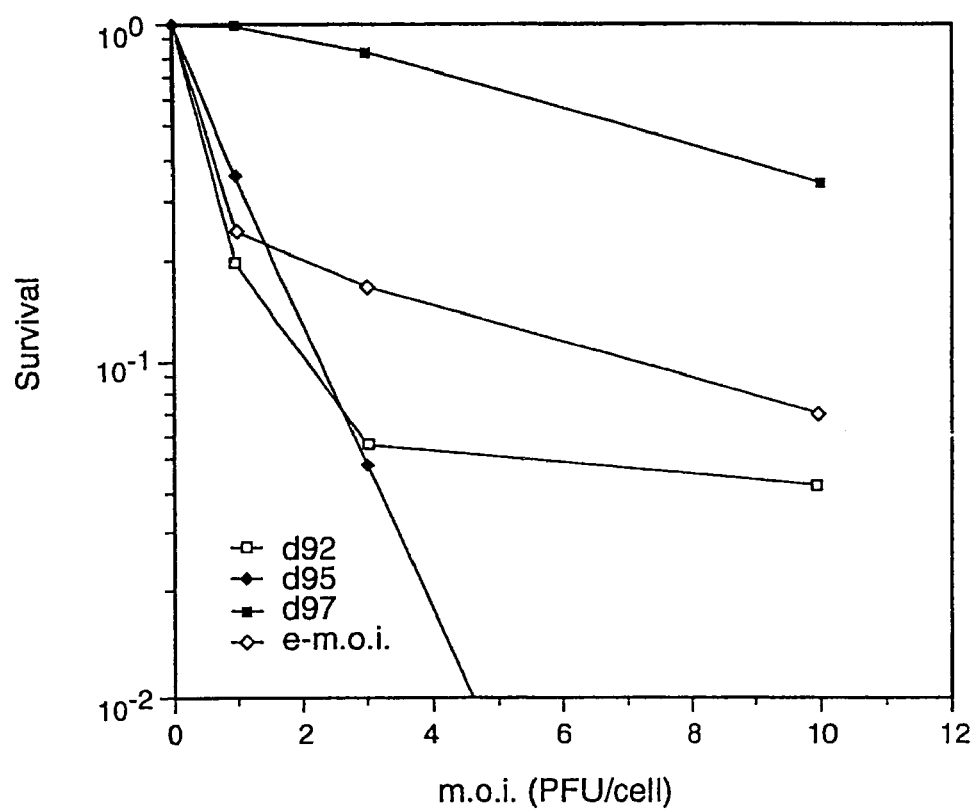
FIG. 1 graphically represents survival of Vero cells infected with several HSV strains at m.o.i.s of 1, 3, and 10.

DETAILED DESCRIPTION OF THE
INVENTION DEFINITIONS

As used herein, including the claims appended hereto, the following terms are defined as follows:

"Herpes simplex virus" (HSV) means both type 1 HSV and type 2 HSV.

"Nonessential HSV gene" means an HSV gene which is nonessential to HSV replication in an ICP4/ICP27 complementing cell line.

"Nonessential region" means a region of a genome of an HSV strain where an exogenous gene may be inserted without interfering with virus function.

An HSV gene product is exogenously supplied to an HSV genome of interest if the gene product is supplied by any means other than by expressing a gene resident within the HSV genome of interest or from an identical HSV genome within the same cell.

"Gene" means an operable unit including both a coding DNA fragment (the DNA fragment which is transcribed, including any polyadenylation sequence or other nontranslated sequence) as well as any regulator operably linked to the coding DNA fragment. "Regulator" means any regulatory region or sequence, including a promoter, enhancer, or other element, which functions to effect transcription of a particular DNA fragment from which the promoter fragment is spatially related.

A gene that is "mutant" or "deficient" is not expressed to a biologically significant level within a cell line not complementing HSV genes. The term includes mutations within the coding region of such a gene such that non-functional gene product is produced or such that no gene product is produced. Additionally, the term includes mutations within regulator regions such that the kinetics of gene expression is sufficiently attenuated so as to produce an insignificant amount of gene product. A gene having an "inactivating mutation" is not expressed to a biologically significant level even in the presence of exogenously supplied HSV gene products.

Viruses

The present invention provides HSV strains having inactivating mutations within both copies of the ICP4 gene (i.e., either the coding region or regulatory regions) and having one or more additional mutations. The mutations can be of any sort, such as the insertion, deletion, or substitution of one or more nucleotides. Preferably, the additional mutations result in the absence of functional gene product of interest, at least in the absence of ICP4, either by disrupting a coding region such that any gene product is defective, and/or by disrupting the regulator (e.g., the promoter or enhancer) such that no appreciable amount of gene product is produced. Where the mutation is the insertion of nucleic acid sequence, the sequence can be a gene or spacer DNA.

Attenuated IE Genes

A first recombinant HSV strain of the present invention has a genome from which, in the presence of the ICP4 gene product, a native immediate early gene of interest is expressed with delayed kinetics (i.e., not expressed during the IE phase of HSV infection). The kinetics of expression can be attenuated such that, in the presence of ICP4, the native immediate early gene of interest is expressed as an early or as a late gene, or not expressed at all. As the IE gene products are variously toxic to cells, in the absence of ICP4, the native immediate early gene of interest preferably is not expressed.

Such a vector is efficiently isolated and grown as described herein, using an exogenous source of ICP4 (or ICP4, ICP27, and/or ICP0 as appropriate), such as packaging cell line complementing ICP4. The presence of the ICP4 product permits the native immediate early gene of interest to be expressed (albeit with delayed kinetics) during packaging, allowing high viral titers to be produced. However, when employed as a gene transfer vector into an animal lacking the HSV ICP4, the native immediate early gene of interest is not expressed, reducing cytotoxicity in vivo and promoting more efficient transgene expression.

The kinetics of any or all of the IE gene products can be so delayed. Preferably, the kinetics of at least the ICP22 and/or ICP47 genes are thus delayed. Such a vector avoids the approximately 5–10 fold reduction in viral titer associated with the immediate early expression of these genes while growing them in packaging cell lines. Thus, such viruses can be grown to at least about $10^{10}$ virus/$10^8$ cells (e.g., about $2 \times 10^{10}$ virus/$10^8$ cells), or even more than about $5 \times 10^{10}$ virus/$10^8$ cells (such about $10^{11}$ virus/$10^8$ cells or even more). Furthermore, such vectors do not express these IE genes in a host lacking ICP4, thereby substantially reducing cytotoxicity in gene transfer applications.

Vectors exhibiting such delayed kinetics of IE gene expression can be produced by any suitable means, such as by mutating a genetic regulator (e.g., a promoter, enhancer, or other regulatory element) of the native immediate early gene of interest. For example, while after the IE phase of infection ICP4 activates many HSV genes (including IE genes), the IE genes are transcribed independently of IE gene products via the VP16-Oct-1 complex as herein described. Therefore, mutation of this sequence attenuates the expression of the IE genes by diminishing their ability to respond to VP16, rendering their expression dependent on the presence of other HSV gene products, notably ICP4. Thus, vectors according to the present invention can exhibit the attenuated IE gene expression by mutation of viral sequences comprising the VP16-Oct1 consensus TAATGARAT sequence, such as sequences consisting of TAATGARAT. These sequences are present within the inverted repeat regions of the HSV genome. Where the genome has mutations ablating the consensus sequence of both inverted repeats, neither ICP22 nor ICP47 is expressed in the absence of ICP4, whereas both genes are expressed as early or late genes in the presence of ICP4.

Triple Mutants

Another HSV vector according to the present invention has a mutation in each of the genes encoding ICP4, ICP27, and at least another HSV gene. Without functional copies of the essential genes, such a vector cannot replicate in non-complementing cells (e.g., within the cells of a host during gene transfer applications), nor does it express any early or late genes, a similar phenotype observed for HSV lacking only ICP4 and ICP27. The third HSV gene mutation can be any HSV gene. However, as only a subset of the HSV genome is expressed in nonceomplementing cells, preferred additional mutations are those which boost viral titer, reduce cytotoxicity, and/or promote prolonged transgene expression. Thus, preferred sites for further mutations are ICP0, ICP22, ICP47, UL39 (i.e., ICP6), and UL41. For example, an HSV lacking functional ICP4, ICP27, and ICP22 imparts fewer cytotoxic effects to host cells than doubly deficient mutants due to the absence of the ICP22 product. Furthermore, an HSV lacking functional ICP4, ICP27, and UL4 1 avoids the host shut-off effect of the tegument protein, UL41.

A preferred triple mutant HSV lacks at least functional ICP4, ICP27, and ICP0 genes. Due to the absence of the ICP0 gene product, this triple mutant virus imparts minimal or no effect on host cell protein synthesis and is relatively non-toxic in comparison with HSV vectors lacking merely ICP4 (e.g., d120) or even HSV vectors lacking ICP4 and ICP27 (e.g., d92). Additionally, the triple mutant virus supports transgene expression for significantly longer than these singly and doubly mutant viruses (e.g., up to several weeks post infection or even longer).

As mentioned herein, the mutations can be of any sort. However, in order to minimize the probability of rescuing a virus having any of these three HSV gene products through recombination with the packaging cell line, the inactivating mutations in ICP4, ICP27, and ICP0 are preferably large deletions (e.g., deletions including most or all of the coding regions); most preferably, the deletions include DNA flanking the coding regions as well.

Further Mutations

In addition to those mutations and properties described above, the HSV of the present invention can have a further mutation (e.g., one or several further mutations). Additional mutations can be within any region of the HSV genome not essential for viral growth within a packaging cell. Preferred further mutations boost viral titer, reduce cytotoxicity, and/or promote prolonged transgene expression. Thus, preferred sites for further mutations are ICP0, ICP22, ICP27, ICP47, UL39 (i.e., ICP6), and UL41. For example, an HSV of the present invention can lack ICP4, ICP27, and ICP0 as herein described and also lack the consensus VP16-Oct1 TAAT-GARAT sequences within the inverted repeats, as herein described. In the absence of exogenously supplied ICP4, no viral genes are expressed, virtually eliminating cytotoxicity in gene transfer applications. However, the virus can be grown to high titers when ICP4, ICP0, and ICP27 are supplied during packaging to complement these mutations in the virus and to promote the transcription of ICP22 and ICP47 as herein described. Further deletion of UL41 and UL39 boosts viral titer by reducing cytotoxicity to the packaging cell line.

Mutations referred to herein, including the claims appended hereto, can be of any conceivable type. For example, a mutation can be a substitution, such as a substitution of one or more amino acids. A mutation can also or instead be a deletion, such as a deletion of all or part of a genetic coding sequence, a regulator of a gene, polynucleotides flanking a gene, spacer DNA, etc. Of course, a mutation can also amount to the insertion of exogenous DNA, such as an insertion of all or part of a genetic coding sequence, a regulator of a gene, polynucleotides flanking a gene, spacer DNA, etc. The insertion itself can be all or part of a coding sequence, a regulatory sequence (e.g., all or part of an exogenous gene), or it can be non-genetic DNA. Examples of exogenous genes which can be thus inserted into the HSV genome include cytokines, cytosine deaminase, thymadine kinase, and others are known in the art.

Method of Production

In view of the additional information set forth herein, the recombinant HSV strains of the present invention can be produced by any suitable method, many of which are known in the art. A common method of engineering recombinant HSV employs a host cell line to direct homologous recombination between a source HSV and DNA mutating vectors (e.g., plasmid vectors, HSV or other viral vectors, etc.) comprising the desired mutant sequence (e.g., deletion, insertion, or substitution) flanked by sequences homologous to the desired locus within the HSV genome. A single round of homologous recombination within the host cell line can introduce one or several desired mutations into the source HSV, and the desired strains can be identified by Southern blotting, assaying for expression of a transgene, or other suitable method.

If homologous recombination is employed to produce the mutant vectors, any HSV vector having regions of homology to the mutating vectors can serve as a source HSV. As each of the vectors of the present invention lacks functioning ICP4 genes, a suitable source vector is an ICP4$^{(-)}$ vector, many of which are known in the art (e.g., d120, DeLuca et al. (1985), supra). Where the vector lacks ICP27 in addition to ICP4, a double mutant lacking both genes is a suitable source HSV, many of which are known in the art (see, e.g., d92, Samaniego et al., supra). Of course, the source vector can lack other genes, or the source vector can be a wild-type HSV strain (requiring the introduction of all desired mutations in one or several rounds of homologous recombination).

For use in the present invention, any appropriate cell line can be employed as a host strain to direct homologous recombination. Regardless of the cell type, the host strain for directing homologous recombination must support the growth of the desired recombinant HSV. Additionally, if a method other than homologous recombination is employed to generate a recombinant virus, a host strain supporting the growth of the desired recombinant virus is nonetheless necessary in order to propagate the resultant virus. The present invention, thus, provides a method of generating the above-mentioned HSV by infecting such a cell line with the HSV, incubating the infected cells in an appropriate medium, and collecting the HSV produced from the cell line. Vero cells (and derivatives thereof) are commonly employed in HSV research; however, other suitable cell types can be used as well.

As mentioned herein, each of these vectors of the present invention lacks functioning ICP4 genes, which are essential for HSV growth. Therefore, for production of the ICP4$^{(-)}$ vectors of the present invention, the cell line must supply complementary levels of ICP4. The present invention contemplates the use of any suitable ICP4 complementing cell line for isolating and propagating the desired recombinant HSV ICP4. An example of such a cell line is E5 (DeLuca et al. (1985), supra). Furthermore, where the HSV strain lacks both ICP4 and ICP27 genes, the cell line must produce complementing amounts of both HSV genes, as both are essential for HSV replication. The present invention contemplates the use of any suitable ICP4/ICP27 complementing cell line for isolating and propagating HSV lacking both ICP4 and ICP27. An example of such a cell line is E26 (Samaniego et al., supra). Furthermore, where the HSV lacks functional ICP4, ICP27 and ICP0, the cell line preferably produces complementary amounts of all three HSV gene products because, as mentioned above, as such triple mutants are not readily obtainable using cells supplying only ICP4 and ICP27. The present invention contemplates the use of any suitable ICP4/ICP27/ICP0 complementing cell line for isolating and propagating HSV lacking the three HSV gene products. An example of such a cell line is F06, described and characterized herein.

Method of Use

As mentioned herein, an HSV of the present invention can have an exogenous gene. Where the HSV has an exogenous gene, the present invention provides a method of expressing the gene within a host cell by infecting the cell with such an HSV. Within the cell, the exogenous gene is expressed to produce either protein or biologically active RNA (e.g., a ribozyme, antisense RNA, etc.). Any of the vectors mentioned herein which contain exogenous genes can be employed to express that gene within the host cell. As many such exogenous genes encode pharmacologically-important products, the present invention also provides a composition for the administration of the mutant virus within a pharmacologically acceptable carrier. Any carrier which can supply the virus without destroying the vector within the carrier is a suitable carrier, and such carriers are well known in the art.

Cell Line

As mentioned above, in order to isolate and grow HSV lacking ICP4, ICP27, and ICP0, a cell line supplying complementing levels of each of these gene products is preferably employed. The present invention provides such a cell line comprising DNA encoding the HSV proteins ICP4, ICP27, and ICP0. The cell line can be a derivative of any cell type capable of supporting HSV growth (e.g., Vero cells or other suitable cells). The cell line preferably supplies each complementing gene product in sufficient quantity to support the growth and replication of HSV strains lacking all three genes. However, because each of the three viral proteins is cytotoxic, the cell line desirably does not overexpress the HSV genes. Preferably, the cell line expresses ICP4, ICP27, and ICP0 in sufficient quantity to support continued cell growth and to enable the cell line to propagate the virus for several passages (e.g., for at least about 5 passages), and more preferably for at least about 10 passages (e.g., for at least about 15 passages); in order to ensure the production of high titer HSV stocks, the cell line most preferably propagates the virus for at least about 20 passages (e.g., at least about 25 passages), or even more.

For replicating the viruses of the present invention, a complementing cell line is preferred over other means of supplying exogenous HSV gene products (e.g., helper viruses, amplicons, etc.) because the genes within a cell line are much less likely to recombine with the viral genome, and because the cellular chromosomes comprising the HSV genes pose no danger of being packaged into HSV virions. As such, the vectors of the present invention together with the cell line of the present invention define a "helper-free" system (i.e., a viral vector system not requiring a helper virus for replication).

In addition to complementing ICP4, ICP27, and ICP0, the cell line can express other genes as well. In order to maintain stable cultures and promote extended passage ability, the cell line preferably contains genes conferring resistance to an antibiotic, and many such genes are known and routinely employed by those of skill in the art (e.g., neomycin phosphotransferase, hygromycin resistance genes, etc.). Cells expressing such genes can be cultured in the presence of antibiotics which ward off contamination by opportunistic, heartier cells.

The ICP4/ICP27/ICP0 complementing cell line of the present invention can be produced by any suitable method, many of which are known in the art. For example, a source cell line can be transformed with a vector (e.g., by viral or retroviral infection, various transfection protocols, etc.) encoding ICP4, ICP27, and/or ICP0 and employing any system which allows for selection of cells harboring the ICP4-, ICP27-, and ICP0-encoding DNA pieces. The genotype of the source cell is not a critical parameter, except that the cell must be able to support HSV growth. Thus, the source cell line can be one which already complements one or more of these three HSV genes (such as those discussed above), or the source cell can express none of them. Regardless of the genotype of the source cell, it is transformed to transiently or stably express the remaining HSV genes. Any suitable method can be employed to select for cells harboring the complementing gene. Thus, for example, the vectors for introducing the HSV genes into the cells can also encode genes conferring resistance to antibiotics (as described above), thus permitting the selection of cells transformed to include the vector (including the HSV genes). Preferably, the vectors include as little as possible non-coding HSV sequences 3' and 5' of the coding sequence in order to avoid introducing homologous sequences into the cell line, thereby reducing or substantially eliminating the probability of rescuing wild-type revertant virus when the cell line is employed. In order to minimize non-coding DNA, preferably the HSV coding sequence(s) within a vector is operably linked to a non-HSV regulator sequence.

The following examples further illustrate the present invention, and, of course, should not be construed as in any way limiting its scope.

EXAMPLES

The examples below refer to the cell line E26, which provides complementing levels of both HSV proteins ICP4 and ICP27. Furthermore, the examples refer to the HSV strain d92, which lacks functional ICP4 and ICP27 genes. Both of these strains are described in Samaniego et al., supra, which is specifically incorporated herein by reference. Moreover, these two strains have been deposited with the American Type Culture Collection under the terms of the Budapest Treaty, as described infra.

Many procedures, such as Southern blots, PCR, vector construction, including direct cloning techniques (including DNA extraction, isolation, restriction digestion, ligation, etc.), cell culture (including cell selection and growing cells to produce plaques), transfection of cells (including $CaCl_2$ and $CaPO_4$ transfection protocols), and β-galactosidase assays are techniques routinely performed by one of ordinary skill in the art (see generally Sambrook et al., *Molecular Cloning, A Laboratory Manual*, Cold Spring Harbor Laboratory, Cold Spring Harbor, N.Y. (1989); Graham et al., *Virol.*, 52, 456–67 (1973)).

Example 1

This example demonstrates the construction and characteristics of a cell line complementing the HSV genes ICP4, ICP27, and ICP0 is demonstrated.

To construct the cell line, the E26 cell line, resistant to G418, was transformed with plasmids pW3-HS8 (Sacks and Schaffer, 1987, J. Virol. 61: 829–839; 5 μg) and pSV2hyg (which encodes resistance to hygromycin; 1 μg). Colonies were selected in the presence of G418 (400 μg/ml) and hygromycin (300 μg/ml) in accordance with standard protocols. All cell lines complemented d92; hence they provided ICP4 and ICP27. Only one of the 80 colonies screened also efficiently complemented both d92 and n212, a previously published ICP0 mutant. This clone, F06, resulted in a 30 fold increase in the number of ICP0 mutant virus plaques.

F06 cells are somewhat more growth impaired than E26 cells, presumably due to the combined toxic effects of ICP4, ICP27, and ICP0. Furthermore, the F06 cell line loses the ability to complement ICP0 mutants after approximately 10 passages if both G418 (400 μg/ml) and hygromycin (300 μg/ml) were not included in the growth maintenance medium. In contrast, when both antibiotics are included in the growth medium, FO6 cells can complement ICP0 mutants for more than about 20 passes. Neither G418 and hygromycin are added when mutant viruses are grown or plaqued on F06 cells.

Example 2

The F06 cell line was used for the isolation of a HSV virus deficient in ICP4, ICP27, and ICP0. The triple mutant HSV resulted from the inactivation of the ICP0 gene from the d92 HSV strain.

Initially the virus 0β was constructed in the following matter. The plasmid pW3-HS8 contains a 4.5 kb SacI to PstI insert which encodes the ICP0 gene. The initiator methionine codon for ICP0 is present in an unique NcoI site in pW3-HS8. 700 bp into the protein coding sequence from NcoI is a unique BamHI site. The sequence contained in the 700 bp NcoI-BamHI fragment was replaced with the BamHI fragment from the plasmid pSC8 that encodes the *E. coli* β-galactosidase gene. This was done after deleting the 700 bp NcoI-Bam HI fragment and modifying the NcoI site in the ICP0 plasmid with synthetic linkers such that it accepts the β-gal-encoding BamHI fragment and puts the ATG in frame with the β-gal protein. This construction puts β-gal under ICP0 control. The resulting plasmid was linearized and cotransfected with wild type virus DNA onto Vero cells. Recombinant plaques were identified by staining with X-Gal. The insertion of β-gal into both ICP0 loci was confirmed by Southern blot analysis.

Figure 3:
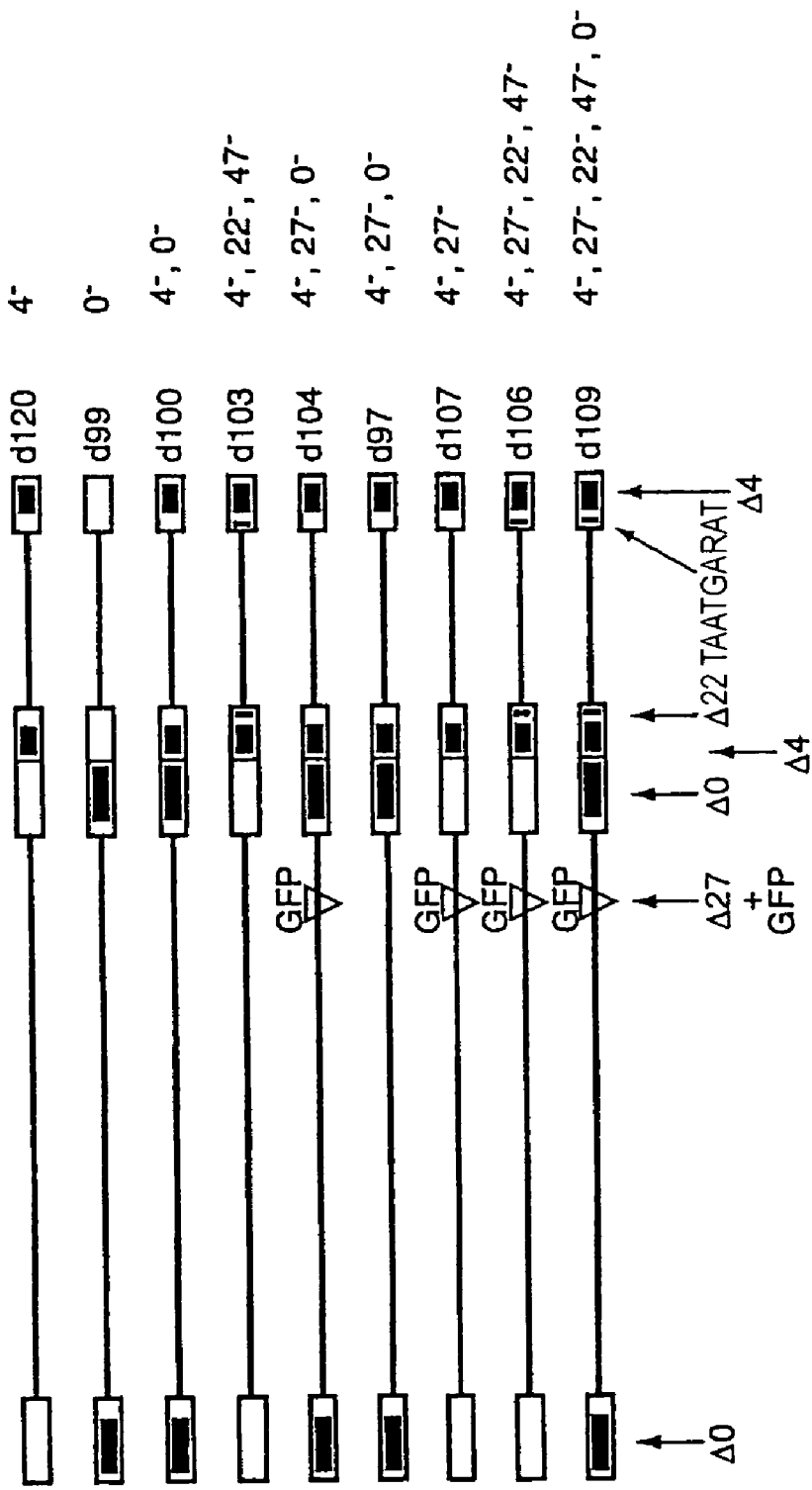
FIG. 3 is a schematic representation of exemplary HSV vectors according to the present invention. The site of deletions and the genotype of the mutant viruses are indicated.
Figure 4A:
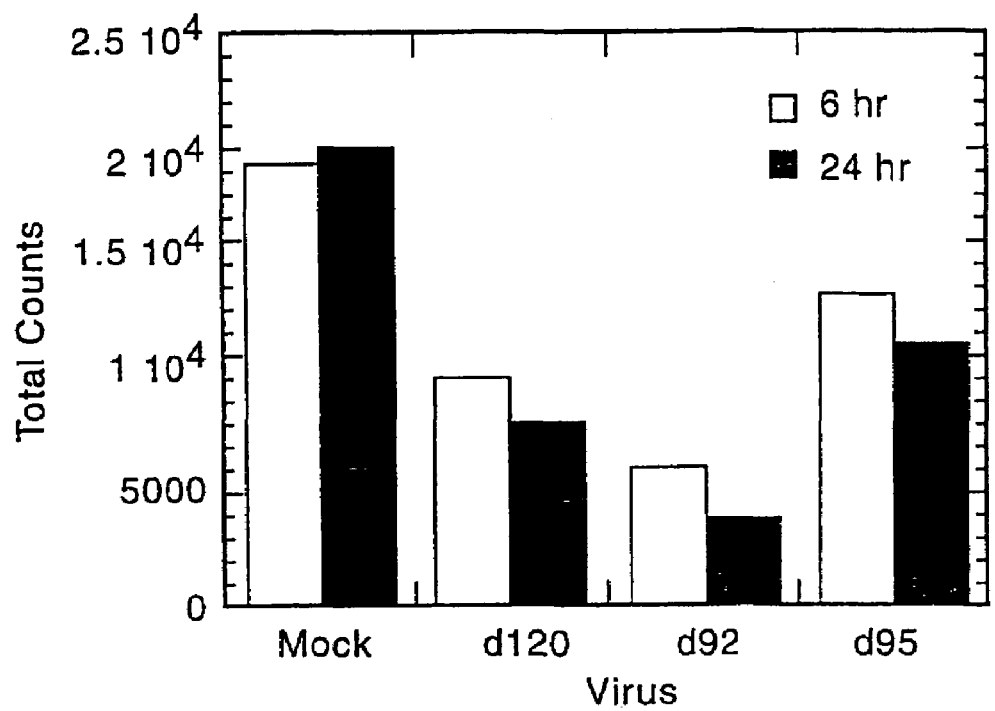
FIGS. 4A–D shows quantitative and qualitative analysis of cellular β-tubulin RNA species.
Figure 4B:
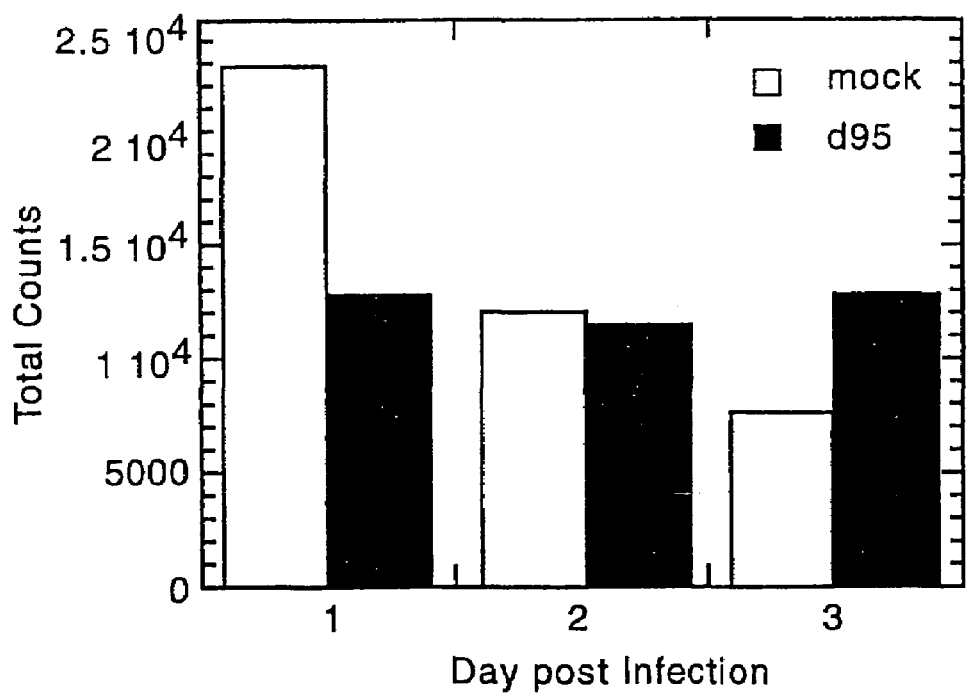
Figure 4C:
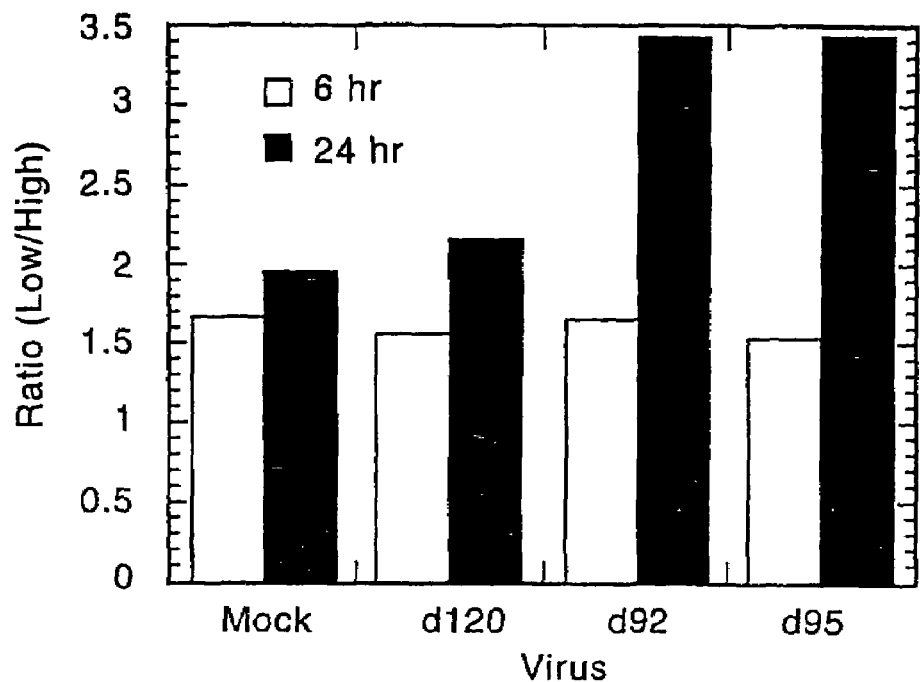
Figure 4D:
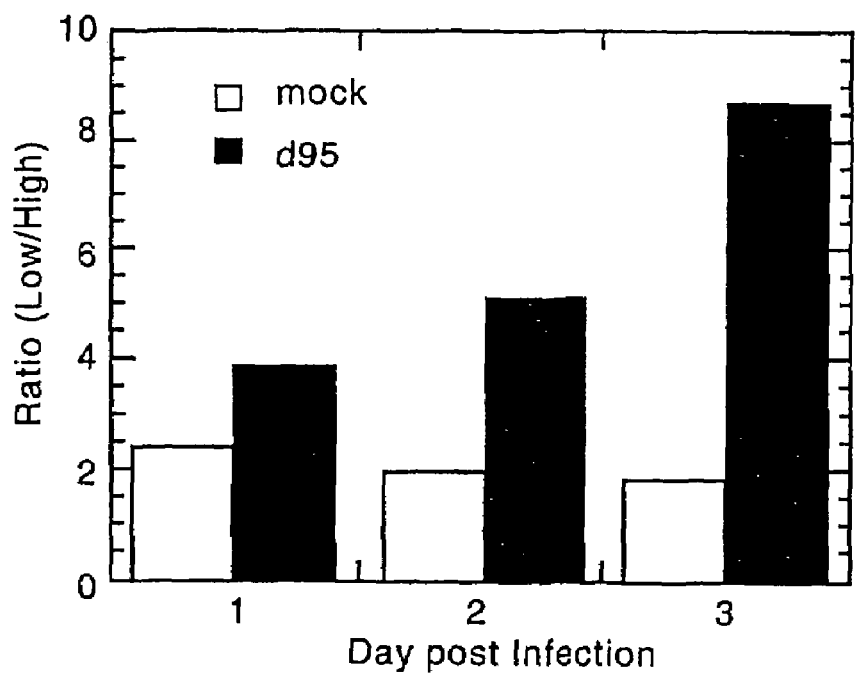

The virus 0β, which contains a deletion of the ICP0 genes, and an insertion of β-galactosidase under the transcriptional control of the ICP0 promoter, was co-infected with d92 on F06 cells. Blue plaques were screened for the presence of the ICP4, ICP27, and ICP0 alleles by plaque assay on different cell lines and by restriction fragment blot analysis. From this the virus d97 (FIG. 3) was isolated.

KOS and the 5dl1.2, d120, d92, d97 HSV mutant strains were inoculated onto Vero cells, first in the presence of cycloheximide for 6 h to allow IE transcripts to accumulate, followed by removal of the cycloheximide and addition of actinomycin D plus $^{35}$S-methionine for 3 h to label translated IE proteins. The data demonstrate that (1) ICP4 was not expressed in d120, d92, d95, or d97; (2) ICP27 was not expressed in 5dl1.2, d92, d95, or d97; (3) ICP0 was not expressed in d97; and (4) β-gal was expressed in d97. $^{35}$S-methionine labeled proteins at 6–9 h post infection in the absence of metabolic inhibitors was also assayed. Data demonstrate that the d97 protein synthesis pattern is similar in the absence and presence of cycloheximide. In other words, the protein synthesis in d97 infected cells was similar to that seen in the absence of de novo protein synthesis, implying that the virus might have a minimal effect on host cell metabolism, and hence cytotoxicity.

Figure 2:
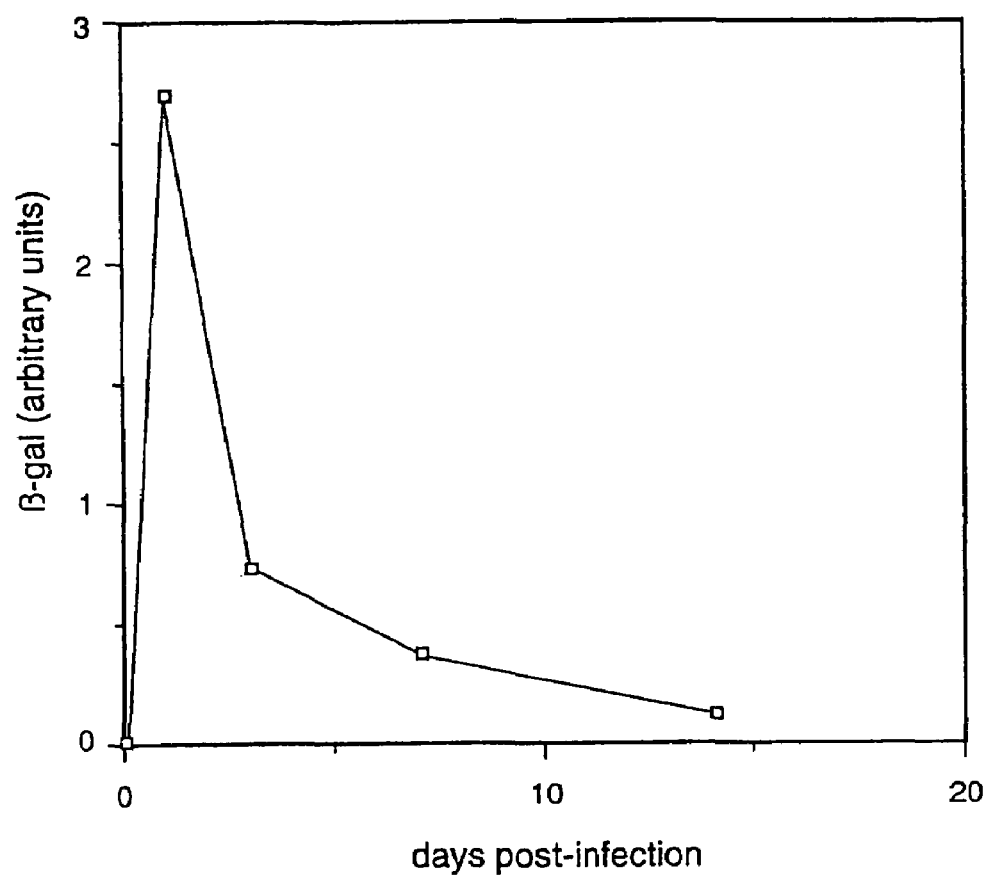
FIG. 2 shows β-gal activity of d97-infected Vero cells over a 14 day period.

To assess toxicity, d97 was compared to d92 and d95 (an HSV lacking ICP4, ICP22, and ICP27 described herein) in colony survival tests. Vero cells were infected with the viruses at m.o.i.s of 1, 3, and 10. At 6 h post infection the cells were trypsinized and plated for surviving colonies. As depicted in FIG. 1, survival was substantially increased by the deletion of ICP0. To further assess the effect of the ICP0 mutants on toxicity, Vero cells were infected with d97 at an m.o.i. of 3 PFU/cell and 3 and 14 days later stained for β-gal. At three days post infection, all the cells were intact and most expressed β-gal. At 14 days, this number decreases but was nonetheless higher than that previously observed for other herpes virus vectors. To quantify the extent of expression, the Vero cells infected with d97 were harvested over the course of 2 weeks and assayed for β-gal activity. Activity peaked at 1 day post infection, and dropped to about 5 percent of this level at 14 days post infection (FIG. 2).

d97 was also used to infect human embryonic lung cells and L7 cells, which express ICP0. β-gal expression was in L7 cells than with Vero cells; however the monolayer was destroyed. These observations demonstrates that ICP0 is a major determinant of vector toxicity, and that a ICP4$^{(-)}$:ICP27$^{(-)}$:ICP0$^{(-)}$ mutant such as d97 will be useful as a gene delivery vector. Uninfected and d97-infected lung cells were stained with X-gal at 2, 4, 8, and 16 days post-infection. β-gal activity could again easily be detected at 16 days post-infection with no observable effects on host cell morphology.

In conclusion, expression from an HSV IE promoter, such as the ICP0 promoter, in d97 is abundant at early times post infection, probably due to activation by VP16 in the virion particle. VP16 turns over with time, and, in the absence of ICP0 to further induce IE promoters, IE gene expression dropped to 5% of the maximum levels at 2 weeks post infection. Despite this reduction, expression remains substantial over time and can be sufficient for a variety of applications. Furthermore, the inclusion of heterologous systems for regulating gene expression in viruses such as d97 provides even further utility to the present invention as disclosed, exemplified, and claimed.

Example 3

The F06 cell line was used for the isolation of a second HSV virus deficient in ICP4, ICP27 and ICP0. The triple mutant HSV resulted from the inactivation of the ICP0 gene from the d92 HSV strain.

A virus containing a deletion of the entire ICP0 gene, including the ICP0 promoter and flanking regions, was co-infected with d120 on E26 cells. Plaques were screened for the presence of the ICP4 and ICP0 alleles by plaque assay on different cell lines and by restriction fragment blot analysis. From this the virus d100 (FIG. 3) was isolated.

Within FO6 cells, d100 was recombined with plasmid containing a deletion of the ICP27 locus and the Green Fluorescent Peptide (GFP) under the control of the HCMV promoter at the ICP27 site. Plaques expressing GFP were screened for the presence of the ICP4, ICP27, and ICP0 alleles by plaque assay on different cell lines and by restriction fragment blot analysis. From this the virus d104 (FIG. 3) was isolated.

The genotype of d104 suggests that the virus will exhibit similar properties as the d97 HSV described above. However, due to the complete deletion of the ICP0 locus, a virus such as d104 should exhibit a lower probability of recombination rescue of ICP0 than the d97 HSV strain.

Example 4

This example demonstrates the isolation of an HSV virus having a genome from which, in the presence of the ICP4 gene product, a native immediate early gene is expressed with delayed kinetics.

A plasmid, pΔTAATGARAT, having a sequence homologous to a portion of the HSV long terminal repeats was engineered to contain deletion of 250 bp, including the consensus TAATGARAT sequence. Within E26 cells, pΔTAATGARAT was recombined with the d120 HSV strain, and plaques were screened for the presence of the deletion by Southern hybridization. From this the virus d103 (FIG. 3) was isolated. The d103 virus was recombined with the d104 virus within FO6 cells. Plaques expressing GFP were screened for the presence of the ICP4, ICP27, and ICP0 alleles and for ΔTAATGARAT by standard assays. From this the viruses d106, d107, and d109 (FIG. 3) was isolated.

In the absence of ICP4, no ICP22 or ICP47 gene product is detected from d103, while in the presence of ICP4 (e.g., within E26 cells), ICP22 and ICP47 are expressed later during infection. However, the virus will express ICP0 and ICP27. In the absence of ICP4, the d106 HSV strain expresses only ICP0, while in the presence of ICP4 and ICP27 (and possible only in presence of ICP4), the ICP22 or ICP47 genes are expressed with delayed kinetics. Similarly, in the absence of ICP4, the d109 HSV strain expresses no native HSV genes, while in the presence of ICP4 and ICP27 (and possible only in presence of ICP4), the ICP22 or ICP47 genes are expressed with delayed kinetics. The IE gene expression profile of d107 is similar to that for d92.

Example 5

This example demonstrates the isolation of a HSV virus deficient in ICP4, ICP27 and ICP22.

An ICP4, ICP27, ICP22 (d95) deficient virus was generated by co-infecting E26 cells with d92 and DMP. DMP is defective for ICP27 and ICP22, by virtue of the 5dl 1.2 and n199 (McCarthy, et al., *J. Virol.*, 63, 1827 (1989); Rice, et al., *J. Virol.*, 69, 5550–59 (1995)) alleles, respectively. Therefore, both viruses used in this cross contain the 5dl1.2 allele, ensuring that the progeny would also contain this allele. The progeny from the co-infection were plaqued on E26 cells. Individual plaques were isolated and screened for the ability to grow on E26, and not on E8 cells, which supply ICP27. This was performed to restrict the further analysis of progeny to isolates that were genetically deficient in ICP4. Isolates that only grew on E26 cells were then screened for the incorporation of the n199 allele by Southern blot hybridization. n199 is marked by a HpaI site, which is part of a linker that specifies the stop codon conferring the ICP22 phenotype.

Southern hybridization confirmed that the isolate lacks both the ICP4 and the ICP22 genes. The plaquing behavior of d95 on E26, E5, and E8 cells is consistent with mutations in both copies of the ICP4 gene and the ICP27 gene.

In order to visualize the IE proteins synthesized in the mutant infected cells and verify the lack of ICP4, ICP27 and ICP22 synthesis, cycloheximide-treated Vero cell monolayers were infected with the indicated viruses at an m.o.i. of 10 PFU/cell and incubated in the presence of cycloheximide for 6 h. The cycloheximide was removed by washing the monolayer, and incubation was continued in the presence of actinomycin D and $^{35}$S-methionine. Under these conditions only the IE proteins are labeled, and ICP4, ICP0, ICP27, and ICP22 were visible in the profiles of KOS infected cells. However, the individual mutants lacked bands corresponding to the intended mutations in the IE genes. More specifically, the data demonstrate that d95 does not synthesize ICP4, ICP27 or ICP22.

To further demonstrate that d95 does not synthesize either ICP4, ICP27, or ICP22, cells were infected with d120, d92, and d95 and were metabolically labeled with $^{32}$P-orthophosphate. Extracts from these infected cells were analyzed by SDS PAGE. ICP27 (in d120-infected cells) and ICP22 (in d120- and d92-infected cells) were readily labeled with 12p. ICP27 was missing in profiles from d95- and d92-infected cells, while ICP22 was missing in the d95-infected cell profile. The lack of ICP22 in d95 was also evident in the $^{35}$S-methionine profile. As expected, ICP4 was not expressed in any host cell infected with d120, d92 or d95.

The effect of prolonged viral and cellular gene expression in d95-Vero infected cells was compared to viral and cellular gene expression patterns from d120- and d92-Vero infected cells. d95-Vero infected cells retained a morphology more closely resembling, but not identical to, uninfected cells. The d95 monolayer was intact at 2 days post infection. In contrast, infection of host cells with d120 or d92 at an m.o.i of 10 PFU/cell were amenable to analysis up to 1 day post infection, and these cell monolayers dispersed by 2 days post infection. Fewer d95-infected than uninfected cells remained at day 2 post infection and many of the d95-infected cells consisted of 2 nuclei in one cytoplasmic boundary. The same general effects on toxicity and cell number were observed on HEL cells, although it was difficult to observe multinucleated cells at this level of resolution.

d92- and d95-infected (m.o.i.=10) Vero cells were labeled with $^{35}$S-methionine at the indicated time post infection and subjected to SDS30 PAGE analysis. ICP22 was clearly evident at time 6 h, 12 h, and 24 h in d92-infected cells, while ICP22 was absent in d95-infected cells. Furthermore, insufficient amounts of protein were detected at 2 and 3 days post infection in d92-infected cells. d120- and d96-infected (d120 and n199 alleles [ICP4$^{(-)}$ICP22$^{(-)}$]) behaved similarly to d92-infected Vero cells with respect to the longevity of protein synthesis. Third, cellular protein synthesis, as well as ICP0 and ICP6 expression, remained high in d95-infected cells up to 3 days infection as compared with mock infected expression.

The abundance of several RNA species was measured by Northern blot analysis to further assess gene expression in d95-infected cells up to 72 hours post infection. ICP0 was abundantly transcribed in the absence of ICP4, but tk was not. The levels of tk in absence of ICP4 are approximately 2–4% of tk levels in the presence of ICP4 (Imbalzano, et al., *J. Virol.*, 65, 565–74 (1991)). ICP0 RNA was slightly increased in size in d92-infected cells relative to d120-infected cells. The abundance of tk RNA was reduced in d92-infected cells relative to d120-infected cells at 6 h post infection (Samaniego, et al., supra). Deletion of ICP22 from the d92 background suppressed these effects. The effect on ICP0 was less evident at 24 h post infection, and that on tk was no longer observed. Consistent with the labeling of cellular proteins in the SDS PAGE results discussed above, the abundance of β-tubulin RNA was greatest in the d95-infected cells, and is comparable to uninfected cells. Therefore, despite the equal loading of total cellular RNA as determined spectrophotometrically and by the ethidium bromide staining patterns of the ribosomal RNA, the abundance of β-tubulin RNA in d120- and d92-infected cells was rescued relative to d95. This implies that the stability or the transcription of these messages is reduced as a consequence of the genes expressed in d120 and d92, and that the further removal of ICP22 relieved this effect. The abundance of all three of the messages in d95-infected cells remained relatively unchanged up to three days post infection. The same patterns of expression of ICP0, tk, and β-tubulin RNA was also seen in HEL cells.

Figure 5A:
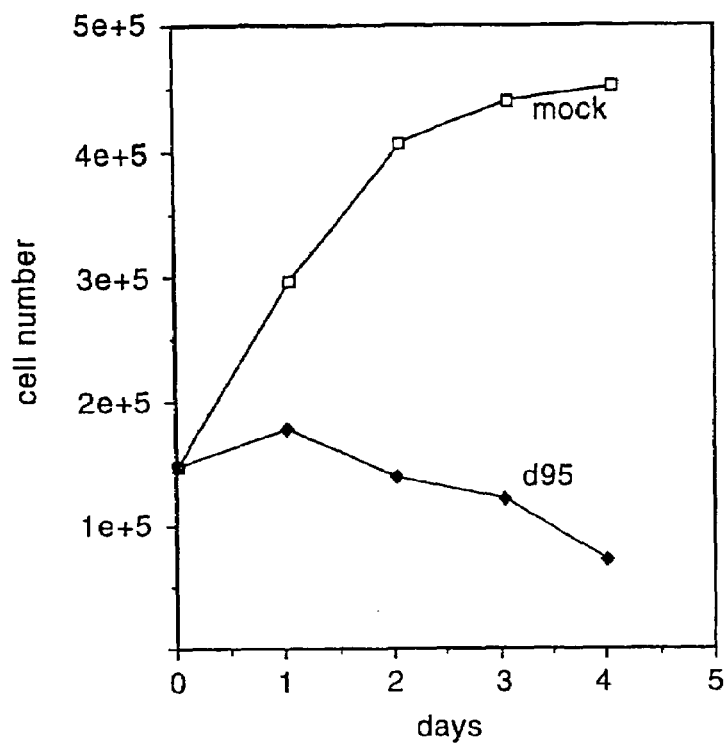
FIGS. 5A–D shows inhibition of cell division and DNA replication in d95-infected cells.

Quantitative analysis of the β-tubulin RNA detected by Northern analysis is indicated in FIGS. 4A–D. At 6 h and 24 h post infection, the levels of β-tubulin RNA was reduced in d120-, d92-, and d95-infected cells, with the lowest reduction seen in d95-infected cells (FIG. 4A). β-tubulin RNA levels in d95-infected cells remained constant for 3 days while β-tubulin RNA declined in uninfected cells over the same period. This is also the case for the levels of ICP0 and tk RNA over this time interval. The simplest interpretation of these data is that HSV proteins expressed from the d95 genome, including ICP0, allow for transcription to continue at a constant rate for three days.

d95-infected Vero cells are inhibited in cellular DNA replication and cell division. While cells infected with d95 do not demonstrate the rapid rounding up and detachment from the monolayer, and continue to express genes on the viral genome for three days, they do not increase in number (FIG. 5A). Vero cells in an uninfected monolayer increased in number for two days. In contrast, d95 infected cells did not, and there was a marginal decrease in the number of cells, suggesting that the growth potential of d95-infected cells was inhibited.

Figure 5B:
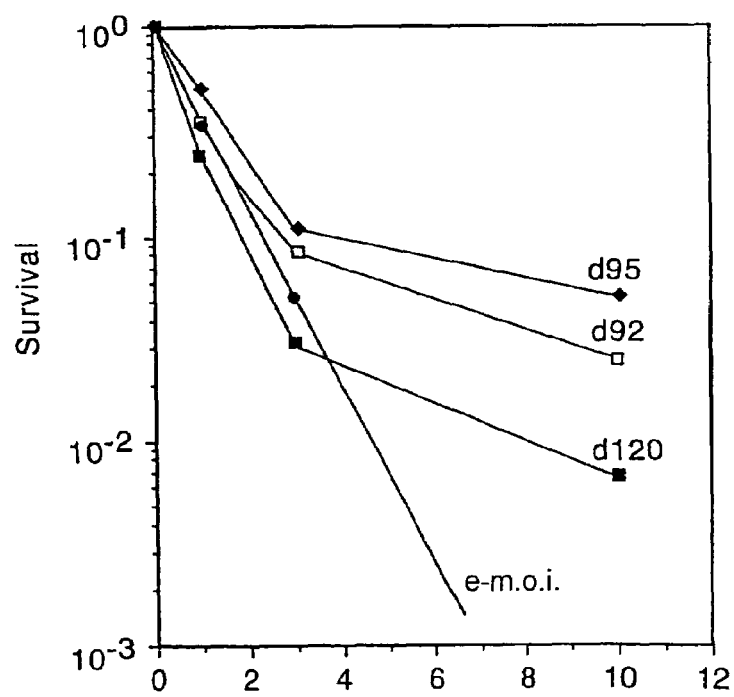
Figure 5C:
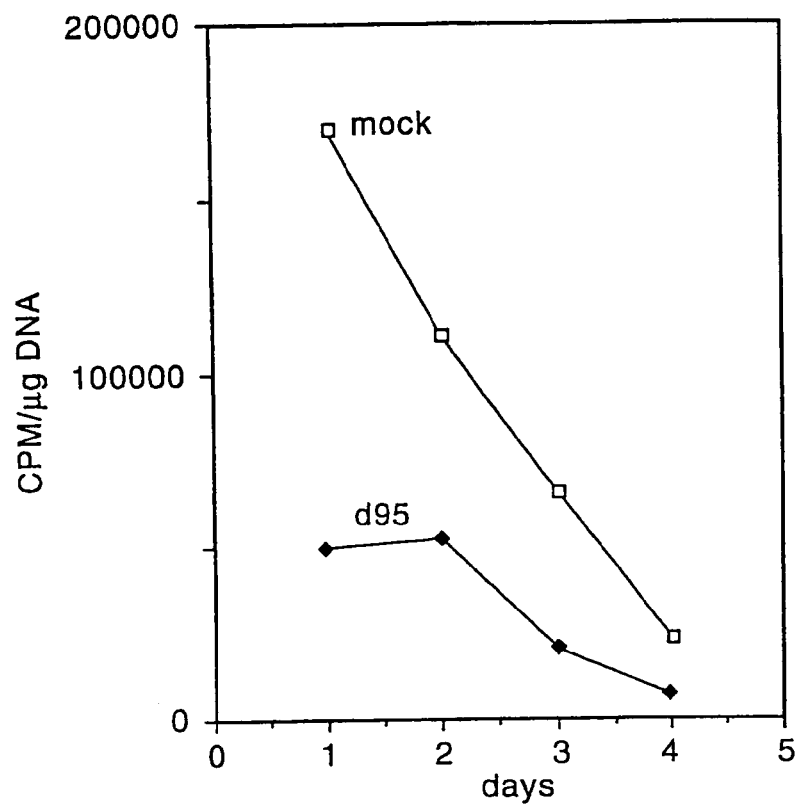
Figure 5D:
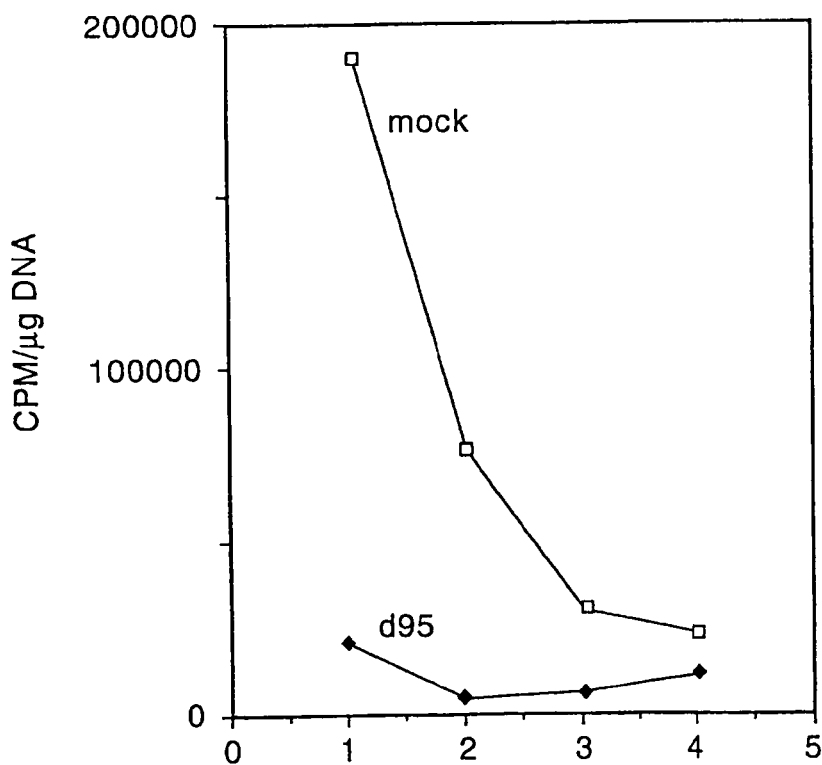

To assess the growth potential of d95 infected cells, two experiments were performed. The first involved infecting monolayers of Vero cells with d120, d92 and d95 at different m.o.i.s, followed by trypsinzing the cells and plating them out for colony forming units (FIG. 5B). The second involves measuring the uptake of $^3$H-thymidine into infected cells (FIG. 5C and FIG. 5D). Using the colony forming assay, d92 inhibited cell viability less than d120. d95 was only marginally less inhibitory than d92, despite the dramatically different appearance of d92- and d95-infected cells discussed above. FIG. 5B also shows the probability of the cells not being infected following inoculation at a given m.o.i. The survival curves indicate that up to an m.o.i of 3, a single PFU is very efficient in inhibiting colony formation. At an m.o.i. of 10, survival is greater than would be expected from the pattern seen at the lower m.o.i.s. This indicates that the inhibitory effects may be saturable or that there are subpopulations of cells that are less susceptible to the inhibitory effects. In summary, all of these viruses had an inhibitory effect on colony forming ability.

It was also determined whether cellular DNA synthesis was inhibited in d95-infected cells. Accordingly, Vero and HEL cells were infected with d95 at an m.o.i. of 10 PFU/cell. At 1, 2, 3, and 4 days post infection, d95-infected and uninfected cells were labeled for 3 hours with $^3$H-thymidine. Following the labeling period, DNA from the cells was isolated and the amount of $^3$H incorporated per microgram of DNA was determined. As is evident in FIGS. 5C and 5D, d95 infection significantly inhibited cellular DNA replication in both Vero and HEL cells, respectively. The drop in uninfected cell labeling at 3 and 4 days post infection is consistent with results of FIG. 5A, probably reflecting contact inhibition.

The other viruses identified in this example could only be analyzed at 1 day post infection. These gave similar results to those obtained for d95 at one day post infection. Therefore, in the absence of ICP4, ICP27, and ICP22, HSV infection results in the loss of cell viability, in part, through the inhibition of DNA synthesis.

The virus d95 abundantly expresses ICP0. Indirect immunofluorescence studies indicate that ICP0 accumulates in the nucleus in large spherical inclusion bodies that can be seen by light microscopy at 2 days post-infection. These observations support the suggestion that such a great accumulation of ICP0, while possibly beneficial for transgene expression, will be deleterious to prolonged host cell survival.

Example 6

This example demonstrates the construction of an HSV strain lacking ICP4, ICP27, and UL41.

ΔSma contains an internal deletion within the UL41 coding region that results in expression of a truncated protein which is not incorporated into virions (Read, et al., 1993, J. Virol. 67:7149–7160). The progeny from a recombinational cross between d92 and ΔSma were plated on 26 cells and plaques were chosen for Southern blot analysis. Isolates were selected on the basis of having deletions in ICP4, ICP27 and UL41. d33 is one such isolate.

Comparison of long continuous protein labeling for uninfected Vero cells, wild type HSV (KOS), d120 (ICP4$^{(-)}$), 5dl 1.2 (ICP27$^{(-)}$), ΔSma (UL41$^{(-)}$), d33 Δ(ICP4:ICP27:UL41), and d92 Δ(ICP4:ICP27) demonstrated that all viruses except ΔSma and d33 show some degree of shut off of host cell protein synthesis. This can be attributed to the lack of a stable vhs activity from these UL41$^{(-)}$ strains. Late genes are not expressed in 5dl 1.2 infected cells, and only ICP0, ICP6, and ICP27 are expressed in d120 infected cells. Viral gene expression is severely impaired in the d92 background. The only discernible viral proteins present in the d92 profile are ICP6 and ICP0. Furthermore when UL41 is mutated in the d92 background (i.e., d33), the observed protein expression profile is similar to that seen in uninfected cells. Despite the dramatic restriction in viral gene expression observed for d33 and d92 in noncomplementing cells, wild-type levels of viral gene expression are observed in the complementing cell line, 26 cells. These viruses can be obtained in quantities discussed within this specification (i.e., titers in excess of $10^9$ PFU/ml). Therefore, this specification discloses the generation of large quantities of these mutant HSV vectors that do not have any wild-type recombinants, and, upon infection of cells, the pattern of protein synthesis resembles that observed in uninfected cells.

Example 7

This example demonstrates the construction of an HSV strain lacking ICP4, ICP27, UL41, and UL39, which strain also contains a transgene.

The plasmid pKXGβ3 was previously used to construct a ΔICP6 recombinant mutant which expresses β-Gal (Goldstein and Weller, 1988, J. Virol. 62:196–205). d33 was cotransfected with pKXGβ3, and the resulting progeny were plated on 26 cells and stained with X-gal. Blue plaques were isolated, analyzed and amplified. The resulting HSV recombinant mutant was d94 Δ(ICP4:ICP27:UL41 :UL39):β-gal.

Wild-type levels of d94 viral gene expression are observed in 26 cells despite a restriction of d94 viral gene expression in Vero cells. This result correlates with the data obtained for the expression profile of d92 and d33 in Vero and 26 cells as described above.

The d94 phenotype was analyzed in noncomplementing cells. An X-Gal stain of Vero cells infected at an m.o.i. of 0.3 PFU d94/cell showed abundant LacZ at two and three days post-infection. The lac-Z marker of d94 is abundantly expressed, and Vero cell morphology is apparently unchanged relative to uninfected cells. Therefore, d94 represents an example of a less toxic HSV recombinant vector that expresses the gene of interest subsequent to target host cell infection.

Figure 6:
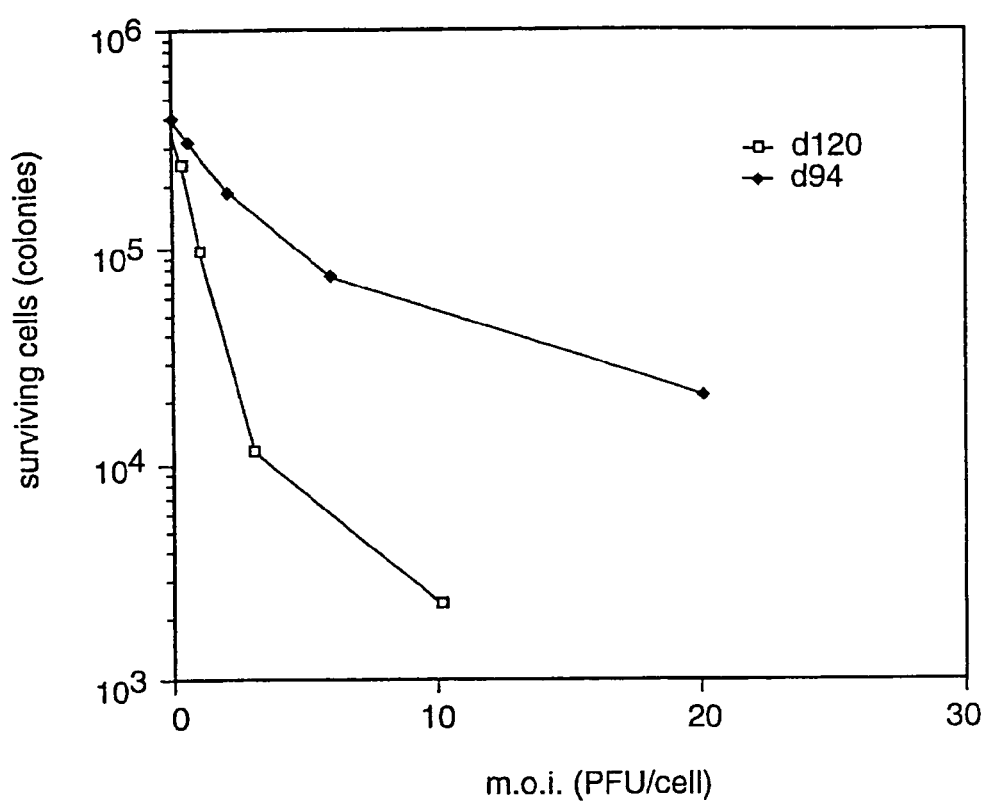
FIG. 6 graphically represents measurements of potential cytotoxicity in d94. Survival of colony forming ability of Vero cells is plotted as a function of input multiplicity.

Recombinant HSV vectors of the present invention show marked reduction in cytotoxicity in comparison with ICP4$^{(-)}$ mutants such as d120, which are currently being used as vectors. Cytotoxic effects are reduced by decreasing the number and type of HSV genes which are expressed subsequent to infection of the host cell, as well as inhibiting post-infection vhs functions. The survival of Vero cells as a function of m.o.i. are shown in FIG. 6. Monolayers of Vero cells were infected with d94 at the m.o.i.s listed in FIG. 6, incubated for 6 hours, and then trypsinized, diluted, and plated out for colonies.

DEPOSIT OF MICROORGANISMS

The following ICP4/ICP27 complementing cell line and HSV-1 ICP4$^{(-)}$ICP27$^{(-)}$ mutant strain were deposited with the American Type Culture Collection (ATCC), 12301 Parklawn Drive, Rockville, Md. 20852, on Apr. 21, 1993, and were converted to deposits under the terms of the Budapest Treaty on Mar. 7, 1996, having been assigned accession numbers as follows:

|                       | Accession No. |
|-----------------------|---------------|
| Cell line "26 cells"  | CRL 11332     |
| HSV-1 strain "d92"    | VR 2406       |

The following ICP4/ICP27/ICP0 complementing cell line was deposited with the American Type Culture Collection (ATCC), 12301 Parklawn Drive, Rockville, Md. 20852, on Jan. 30, 1996 under the terms of the Budapest Treaty and assigned the following accession number:

|                 | Accession No. |
|-----------------|---------------|
| Cell line "FO6" | CRL 12028     |

The following HSV-1 ICP4$^{(-)}$ICP27$^{(-)}$ additional IE genes mutant strains were deposited with the American Type Culture Collection (ATCC), 12301 Parklawn Drive, Rockville, Md. 20852, on Jan. 30, 1996 under the terms of the Budapest Treaty, and assigned accession numbers as follows:

|                      | Accession No. |
|----------------------|---------------|
| HSV-1 strain "d95"   | VR 2523       |
| HSV-1 strain "d97"   | VR 2524       |

All references cited herein are hereby incorporated by reference.

While this invention has been described with emphasis upon preferred embodiments, it will be obvious to those of ordinary skill in the art that the preferred embodiments can be varied. It is intended that the invention may be practiced otherwise than as specifically described herein. Accordingly, this invention includes all modifications encompassed within the spirit and scope of the appended claims.

What is claimed is:

1. An isolated herpes simplex virus (HSV) or HSV genome having a mutation of a native TAATGARAT sequence such that, in the presence of HSV ICP4 gene product, a native immediate early gene is expressed from the genome with delayed kinetics, the genome having a further inactivating mutation of each of the copies of the gene encoding ICP4.

2. The HSV or HSV genome of claim 1, which includes a further inactivating mutation in at least one of the ICP0, ICP22, ICP27, ICP47, ICP6, or UL41 loci.

3. The HSV or HSV genome of claim 2, wherein the further mutation affects the ICP0 locus.

4. The HSV or HSV genome of claim 1, wherein the genome includes an exogenous gene.

5. The HSV or HSV genome of claim 2, wherein the genome includes an exogenous gene.

6. The HSV or HSV genome of claim 3, wherein the genome includes an exogenous gene.

7. The HSV or HSV genome of claim 4, exogenous gene encodes a cytokine.

8. The HSV or HSV genome of claim 5, wherein the exogenous gene encodes a cytokine.

9. The HSV or HSV genome of claim 6, wherein the exogenous gene encodes a cytokine.

10. A method of expressing a polynucleotide within a cell including infecting the cell with an HSV or HSV genome of claim 4.

11. A method of expressing a polynucleotide within a cell including infecting the cell with an HSV or HSV genome of claim 5.

12. A method of expressing a polynucleotide within a cell including infecting the cell with an HSV or HSV genome of claim 6.

13. A composition for the administration of a mutant virus including an HSV or HSV genome of claim 1 and a pharmacologically acceptable carrier.

14. A composition for the administration of a mutant virus including an HSV or HSV genome of claim 2 and a pharmacologically acceptable carrier.

15. A composition for the administration of a mutant virus including an HSV or HSV genome of claim 3 and a pharmacologically acceptable carrier.

16. A composition for the administration of a mutant virus including an HSV or HSV genome of claim 4 and a pharmacologically acceptable carrier.

17. A composition for the administration of a mutant virus including an HSV or HSV genome of claim 5 and a pharmacologically acceptable carrier.

18. A composition for the administration of a mutant virus including an HSV or HSV genome of claim 6 and a pharmacologically acceptable carrier.

19. A composition for the administration of a mutant virus including an HSV or HSV genome of claim 7 and a pharmacologically acceptable carrier.

20. The HSV or HSV genome of claim 2, wherein the further mutation affects the ICP22 locus.

21. The HSV or HSV genome of claim 2, wherein the further mutation affects the ICP27 locus.

22. The HSV or HSV genome of claim 2, wherein the further mutation affects the ICP47 locus.

23. The HSV or HSV genome of claim 2, wherein the further mutation affects the ICP6 locus.

24. The HSV or HSV genome of claim 2, wherein the further mutation affects the UL41 locus.

25. The HSV or HSV genome of claim 4, wherein the exogenous gene encodes a cytosine deaminase.

26. The HSV or HSV genome of claim 4, wherein the exogenous gene encodes a thymidine kinase.

27. The HSV or HSV genome of claim 5, wherein the exogenous gene encodes a cytosine deaminase.

28. The HSV or HSV genome of claim 5, wherein the exogenous gene encodes a thymidine kinase.

29. The HSV or HSV genome of claim 6, wherein the exogenous gene encodes a cytosine deaminase.

30. The HSV or HSV genome of claim 6, wherein the exogenous gene encodes a thymidine kinase.

* * * * *

UNITED STATES PATENT AND TRADEMARK OFFICE
CERTIFICATE OF CORRECTION

PATENT NO. : 7,078,029 B2  Page 1 of 1
APPLICATION NO. : 10/427739
DATED : July 18, 2006
INVENTOR(S) : DeLuca It is certified that error appears in the above-identified patent and that said Letters Patent is hereby corrected as shown below:

IN THE SPECIFICATION:

In Column 18, line 1: "7. The HSV or HSV genome of claim 4, exogenous gene encodes a cytokine." should read --7. The HSV or HSV genome of claim 4, wherein the exogenous gene encodes a cytokine.--

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,078,029 B2 | Page 1 of 1 |
| APPLICATION NO. | : 10/427739 | |
| DATED | : July 18, 2006 | |
| INVENTOR(S) | : DeLuca | |

It is certified that error appears in the above-identified patent and that said Letters Patent is hereby corrected as shown below:

IN THE SPECIFICATION:

Column 1
Line 12, after the cross-reference to related applications, please insert the following paragraph:

--STATEMENT REGARDING FEDERALLY SPONSORED RESEARCH AND DEVELOPMENT
 This invention was made in part with Government support under Grant Numbers AI 027431 awarded by the National Institutes of Health. The United States Government may have certain rights in this invention.--

Signed and Sealed this

Twentieth Day of March, 2007

JON W. DUDAS
*Director of the United States Patent and Trademark Office*